United States Patent [19]

Motoyama, deceased et al.

[11] Patent Number: 5,128,131

[45] Date of Patent: Jul. 7, 1992

[54] PROCESS FOR PREPARING A WATERSOLUBLE COMPOSITION CONTAINING GINKGO LEAF EXTRACTS

[75] Inventors: Shimesu Motoyama, deceased, late of Asaka, by Kazuko Motoyama, Kazuhiro Motoyama, legal representative; Seiichi Umeda; Yukihiro Saito, both of Saitama, all of Japan

[73] Assignee: Freund Industrial Co., Ltd., Tokyo, Japan

[21] Appl. No.: 431,022

[22] Filed: Nov. 2, 1989

[30] Foreign Application Priority Data

Nov. 4, 1988 [JP] Japan .................. 63-279156
Oct. 5, 1989 [JP] Japan .................. 1-261184

[51] Int. Cl.⁵ .................. A61K 35/78; A61K 31/715; A01N 43/04
[52] U.S. Cl. .................. 424/195.1; 514/54; 514/464
[58] Field of Search .................. 514/464, 54; 424/195.1

[56] References Cited

U.S. PATENT DOCUMENTS

| | | | |
|---|---|---|---|
| 775,249 | 11/1904 | Roberts | 424/195.1 |
| 1,631,384 | 6/1927 | Richmond | 424/195.1 |
| 2,008,238 | 10/1933 | Rockmuhl | 424/195.1 |
| 4,454,113 | 6/1984 | Hemker | 424/63 |
| 4,501,734 | 2/1985 | Tanaka | 514/198 |
| 4,886,904 | 12/1989 | Tanaka | 560/249 |
| 4,892,883 | 1/1990 | Chatterjee | 514/464 |
| 4,898,727 | 2/1990 | Osada | 424/76.1 |

FOREIGN PATENT DOCUMENTS

1767098 5/1972 Fed. Rep. of Germany.
2117429 10/1972 Fed. Rep. of Germany.

OTHER PUBLICATIONS

King J. American Dispensatory 8th Ed 1870 pp. 822-823.
Remington 3rd Ed. Practice of Pharmacy 1895 pp. 199-205.
Steinmetz, Codex Vegetabilis 1957 1038, 1118.
Weinges & Bahr, Liebigs Ann Chem. 724 214-216 1969.
Remingtons Pharmaceutical Sciences 15th Ed. 1975 pp. 242-243, 1512-1514.
Kirlk Othmer Encyclopedia of Chemical Technoogy vol. 16 3rd Ed. pp. 314-vol 1 p. 888-889.

*Primary Examiner*—Johnnie R. Brown
*Assistant Examiner*—Ralph Gitomer
*Attorney, Agent, or Firm*—Kane, Dalsimer, Sullivan, Kurucz, Levy, Eisele and Richard

[57] ABSTRACT

A composition containing an extract obtained by a water-containing organic solvent, comprising: (a) an extract containing active ingredients including flavone glycoside or biflavone almost insoluble in water, said extract being obtained for ginkgo plant tissues by extraction with a water-containing organic solvent, and at least one of (b) a water-soluble high-molecular substance and (c) a fatty acid ester of polyglycerol. This composition can be formulated into preparations not containing ethanol, i.e. solid preparations including tablets, granules, and powder preparations, or non-alcoholic liquid preparations such as drinkable preparations and syrups, in such a way that the extract contained is well absorbed through the digestive tract.

6 Claims, 4 Drawing Sheets

PROCESS FOR PREPARING A WATERSOLUBLE COMPOSITION CONTAINING GINKGO LEAF EXTRACTS

BACKGROUND OF THE INVENTION

1. Field of the Invention

This invention relates to a composition containing an extract obtained by extraction with a water-containing organic solvent, which has a high bioavailability and can be formulated into various preparations including tablets, granules, powder preparations, drinkable preparations, and syrups, and also to a process for preparing said composition.

2. Prior art

In France, Germany, etc., remedial preparations containing, as active ingredient, an extract obtained from plant tissues such as ginkgo leaves by extraction with a water-containing organic solvent have hitherto been used widely for the purpose of improving metabolism of cerebral circulation.

It is known that the above extract obtained by extraction with a water-containing organic solvent has such pharmacological actions as relaxation of smooth muscles of blood vessels contracted owing to stress, tension, etc., thereby reducing resistance in peripheral arteries and cerebral circulatory system; and vasodilation and increasing of blood flow velocity, thereby increasing blood flow in the pacillary tissues. Said extract is also known to have a pharmacological action of lowering viscosity of the blood in the arteries and veins, thereby smoothing the blood flow, with the result that disorder in the peripheral blood vessels and cerebral blood vessels is improved.

In order to administer the above extract obtained by extraction with a water-containing organic solvent to elderly people, or minors, or to patients with liver diseases, it is desirable to formulate it into preparations not containing ethanol. That is to say, it is necessary to formulate it into solid preparations including tablets, granules, and powder preparations, or liquid preparations such as drinkable preparations and syrups, in such a way that no ethanol is used, yet the extract contained is well absorbed through the digestive tract.

However, the above-mentioned extract obtained by extraction with a water-containing organic solvent has such property that it is soluble in water-containing organic solvents such as water-containing acetone, water-containing methyl ethyl ketone, water-containing methanol and water-containing ethanol, but practically insoluble in water. Thus, it is possible to formulate the extract into liquid preparations such as tinctures, spirits, and elixirs, as ethanol is used in these preparations as one of the solvents.

However, it has been impossible to formulate it into non-alcoholic liquid preparations such as non alcoholic drinkable preparations and syrups.

When the above extract obtained by extraction with a water-containing organic solvent is used in easy-to-take solid preparations such as tablets, granules and powder preparations, the absorption becomes poor. The reason is that, to have the active ingredients of the extract absorbed into the human body, it is necessary for the active ingredients to be dissolved or emulsified in the digestive tract.

In making this invention, the above problems were taken into consideration, and thus the purpose of this invention is to provide a composition which contains an extract obtained by extraction with a water-containing organic solvent and which has a high bioavailability and can be formulated into various forms of preparations including tablets, granules, powder preparations, drinkable preparations and syrups.

Another purpose of this invention is to provide a process for preparing said composition containing an extract obtained by extraction with a water-containing organic solvent.

SUMMARY OF THE INVENTION

The composition of this invention is one whose main components are an extract containing active ingredients almost insoluble in water which is obtained from plant tissues by extraction with a water-containing organic solvent, and a water-soluble high-molecular substance and/or a fatty acid ester of polyglycerol. As plant tissues, there are exemplified ginkgo leaves, balloon flower (Platycodon grandiflorum A. DC.), carrots, roots of Scopolia japonica Maximowicz, etc. In the extract from ginkgo leaves, there are contained flavone glycoside, biflavone, etc. as active ingredients almost insoluble in water, while in the extracts from carrots and balloon flower (Platycodon grandiflorum A. DC.) there are contained saponins. Meanwhile, the extract from the roots of Scopolia japonica Maximowicz contains tropane alkaloid, coumarin glycoside, etc. The above-mentioned extracts obtained from plant tissues mean those which are obtained from said plant tissues by extraction in a conventional manner with a water-containing organic solvent such as water-containing methanol, water-containing ethanol, water-containing acetone, and water-containing methyl ethyl ketone, and from which the water-containing solvent has been distilled off.

As water-soluble high molecular substance, there are no particular restrictions provided it is a pharmaceutically acceptable substance, and those desirable include gum arabic, xanthan gum, guar gum, gum extracted from tamarind seeds, and sodium alginate. Of these, gum arabic is especially preferable.

As for fatty acid ester of polyglycerol, any such ester may be used. However, it is desirable to use monostearate, monooleate or monolaurate of decaglycerin; monostearate, monooleate or monolaurate of hexaglycerin; and monolaurate of tetraglycerin, provided hydrophilic lipophilic balance (HLB) of the ester is 10 or higher.

To prepare the composition of this invention, an extract obtained as above by extraction with a water-containing organic solvent, and a water-soluble high-molecular substance and/or a fatty acid ester of polyglycerol are mixed first. When, in this process, the two (or three) components are first dissolved and evenly mixed in a water-containing lower alcohol, and then the solvent (water-containing lower alcohol) is distilled off, followed by drying, there is obtained a composition whose active ingredients have an improved solubility and a very high bioavailability. As a water-containing lower alcohol to be used in this process, it is desirable to use an aqueous solution of alcohol with 20–45 v/v % content of lower alcohol. As lower alcohol, there are exemplified methanol, ethanol, isopropanol, etc., of which ethanol is especially preferable.

Concrete methods of preparation include the following:

(1) An extract obtained by extraction with a water-containing organic solvent is dissolved in a water-containing lower alcohol. To this are added a water-soluble high-molecular substance and/or a fatty acid ester of polyglycerol, and then water to make a solution or an emulsion. After that, the solvent in the solution (or emulsion) is distilled off by a publicly-known method such as spray-drying method or ventilation-drying method.

(2) A method in which the extract obtained by extraction with a water-containing organic solvent is structurally modified by coating the surface of the extract with a water-soluble high-molecular substance and/or a fatty acid ester of polyglycerol with use of a surface modification apparatus for fine particle.

(3) A water-soluble high-molecular substance and/or a fatty acid ester of polyglycerol, and water are added to a solution of an extract obtained by extraction with a water-containing organic solvent, and a water soluble high-molecular substance and/or a fatty acid ester of polyglycerol in a water-containing lower alcohol; or to a solution of an extract obtained by extraction with a water-containing organic solvent in a water containing lower alcohol. Then, the solution (or emulsion) obtained is adsorbed to an excipient or excipients in a fluidized bed, and then dried.

Next, the mixture, prepared as above, of an extract obtained by extraction with a water-containing organic solvent, and a water-soluble high-molecular substance and/or a fatty acid ester of polyglycerol is mixed with a publicly-known excipient or excipients, and then a binder is added. The mixture thus prepared is then granulated in a fluidized bed, whereby granules of the composition of this invention are obtained. The granules can also be tableted after adding a suitable lubricant. Either a water-soluble high-molecular substance or a fatty acid ester of polyglycerol may be used, but when both are used, better results are obtained in many cases as compared with the use of only one of the two.

The solid preparations, made as above, of the composition of this invention are soluble in water or dispersible in water in fine particles, thereby making it easy to be absorbed into the digestive tract, and as a result, a bioavailability equal to that of conventional alcohol-containing liquid preparations is obtained.

In addition to excipient, binder, lubricant, and disintegrator, there may be added to the composition of this invention other additives generally accepted for foods and pharmaceuticals. These include sweetener and perfume which are used to improve taste, and surfactant used to stabilize dispersion. The product may also be coated.

The composition of this invention can also be dissolved or emulsified in water without the use of ethanol or with the use of a very small amount (1%) of ethanol, thereby making it possible to formulate it into liquid preparations having a good absorbency in the digestive tract. To the liquid preparations thus made, there may also be added sweeteners such as saccharose, glucose, sorbitol, maltitol, stevia, and aspartame, and preservatives such as sodium benzoate, and p-hydroxy benzoate. The following Examples and accompanying drawings are given to further illustrate this invention.

DETAILED DESCRIPTION OF THE PREFERRED EMBODIMENT

EXAMPLE 1

Figure 1:
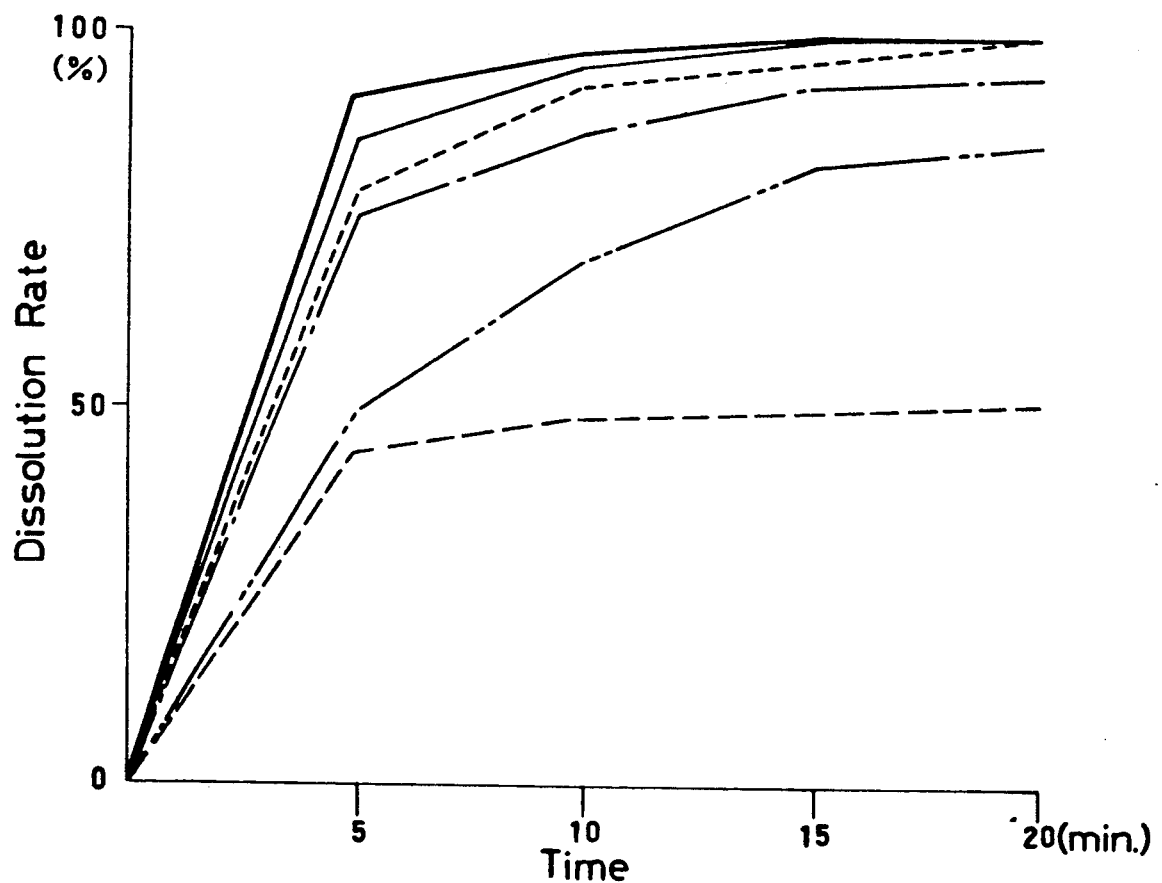
FIG. 1 shows, by graph, the results of dissolution tests of the compositions each containing an extract obtained with a water-containing organic solvent, which are shown in Examples of this invention.

The following Compositions 1-10, with components as mentioned below, each containing an extract obtained by extraction with a water-containing organic solvent were prepared:

(1) Composition 1, containing an extract obtained by extraction with a water-containing organic solvent In 1 l of a water-containing ethanol with 30 v/v % alcohol content, were dissolved 100 g of an extract obtained from ginkgo leaves by extraction with a water-containing organic solvent, and 100 g of gum arabic, and after that, the solvent in the solution was distilled off by the spray-drying method, whereby a composition in powder form was obtained.

(2) Composition 2, containing an extract obtained by extraction with a water-containing organic solvent In 1 l of a water-containing ethanol with 30 v/v % alcohol content, were dissolved 100 g of an extract obtained from ginkgo leaves by extraction with a water-containing organic solvent and 100 g of guar gum, and after that, the solution was dried by the ventilation-drying method. The resultant lumps were crushed by hammer mill, whereby a composition in powder form was obtained.

(3) Composition 3, containing an extract obtained by extraction with a water-containing organic solvent In 100 ml of a water-containing ethanol with 40 v/v % alcohol content, was dissolved 100 g of an extract obtained from ginkgo leaves by extraction with a water-containing organic solvent. To this solution were added 100 g of xanthan gum and 900 ml of water, and the mixture was stirred in a homogenizer at a high speed so as to obtain an emulsion.

After that, the solvent in the emulsion was distilled off by the spray-drying method, whereby a composition in powder form was obtained.

(4) Composition 4, containing an extract obtained by extraction with a water-containing organic solvent In 100 ml of water-containing ethanol with 40 v/v % alcohol content, was dissolved 100 g of an extract obtained from ginkgo leaves by extraction with a water-containing organic solvent. To this solution were added 100 g of sodium alginate and 900 ml of water, and the mixture was stirred in a homogenizer at a high speed to obtain an emulsion. After that, the solvent in the emulsion was distilled off by the ventilation-drying method, and the lumps obtained were crushed by hammer mill, whereby a composition in powder form was obtained.

(5) Composition 5, containing an extract obtained by extraction with a water-containing organic solvent A mixture of 100 g of an extract from ginkgo leaves by extraction with a water-containing organic solvent and 200 ml of a 10 v/v % aqueous solution of gum arabic was subjected to fine disintegrating and coating with a surface modification apparatus for fine particle, to obtain a composition in powder form.

(6) Composition 6, containing an extract obtained by extraction with a water-containing organic solvent A mixture of the solution in water-containing ethanol prepared in (1) above (or emulsion made in (3) above) and 1.8 kg of lactose was granulated in a fluidized bed, whereby a composition in granules was obtained. By adding a suitable quantity of a lubricant, the granules could be made into tablets by the direct tableting method.

(7) Composition 7, containing an extract obtained by extraction with a water-containing organic solvent The procedure of (1) above (Composition 1) was followed except for using 80 g of decaglycerin monolaurate in place of 100 g of gum arabic.

(8) Composition 8, containing an extract obtained by extraction with a water-containing organic solvent The procedure of (1) above (Composition 1) was followed except for using 80 g of gum arabic and 50 g of decaglycerin monooleate in place of 100 g of gum arabic.

Next, to 20 mg each of above Compositions 1-5, 7 and 8 were added 375 mg of lactose, and 5 mg of a fatty acid ester of sucrose as lubricant. Then, each mixture was tableted, whereby 400 mg of tablets was obtained respectively. As for Composition 6, it was tableted, without adding anything, to obtain 400 mg of tablets.

(9) Comparison Example 1

To 10 mg of an extract obtained from ginkgo leaves by extraction with a water-containing organic solvent were added 385 mg of lactose and 5 mg of a fatty acid ester of sucrose, and the mixture was tableted to obtain 400 mg of tablets.

(10) Comparison Example 2

An extract obtained from ginkgo leaves by extraction with a water-containing organic solvent was tableted, without adding anything, to obtain 400 mg of tablets. However, the tablets obtained were not soluble in water.

Dissolution test

A dissolution test was performed, by the method and with the apparatus described in the Japanese Pharmacopoeia, for each lot of tablets obtained from Compositions 1-5, 7 and 8, and Comparison Example 1. In this test, the paddle method was used, under the following conditions: Purified water 500 ml, 3 tab., wavelength ($\lambda$max) 266 nm, number of revolutions of spindle 100 rpm, and temperature of water 37° C.

Results obtained are shown in FIG. 1. As is clear from these results, the tablets from Comparison Example 1 were slightly soluble, while the tablets from Compositions 1-5, 7 and 8 each showed a good dispersibility in water. The "dissolution rate" includes both what was dissolved into solution and what came into emulsion, the term being used in the same way hereafter.

Clinical Experiment

A double blind experiment was performed using tablets made from Compositions 1, 7 and 8 and tablets of Comparison Example 1, covering 128 patients with disturbance in cerebral circulation. The tablets were given orally (before meal: 4 tablets at a time; 3 times/day).

As a result of administration for one month, improvement was seen, as compared with the conditions before administration, in 29 patients (67.4%) out of 43 receiving tablets of Composition 1, in 15 patients (68.2 out of 22 receiving tablets of Composition 7, and in 17 patients (73.9%) out of 23 receiving tablets of Composition 8. On the other hand, in the group receiving tablets of Comparison Example 1, improvement was seen in 13 patients (32.5%) out of 40. Thus, as compared with the tablets of Comparison Example 1, excellent results were seen in tablets of Composition 1 with +34.9%, in tablets of Composition 7 with +35.7%, and in tablets of Composition 8 with +41.4%, showing that each of these 3 compositions has a high bioavailability.

EXAMPLE 2

(11) Composition 9, containing an extract obtained by extraction with a water-containing organic solvent In 100 g of liquid extract (solid content 15%) obtained from ginseng by extraction with a water-containing ethanol with 25 v/v % alcohol content, was dissolved 10 g of gum arabic, and after that, the solvent in the solution was distilled off by the spray-drying method, whereby a compound in powder form was obtained.

(12) Comparison Example 3

The solvent in 100 g of liquid extract (solid content 15%) obtained from ginseng by extraction with a water-containing ethanol with 25 v/v % alcohol content was distilled off by the spray-drying method, whereby a powder product was obtained.

Dissolution test

Figure 2:
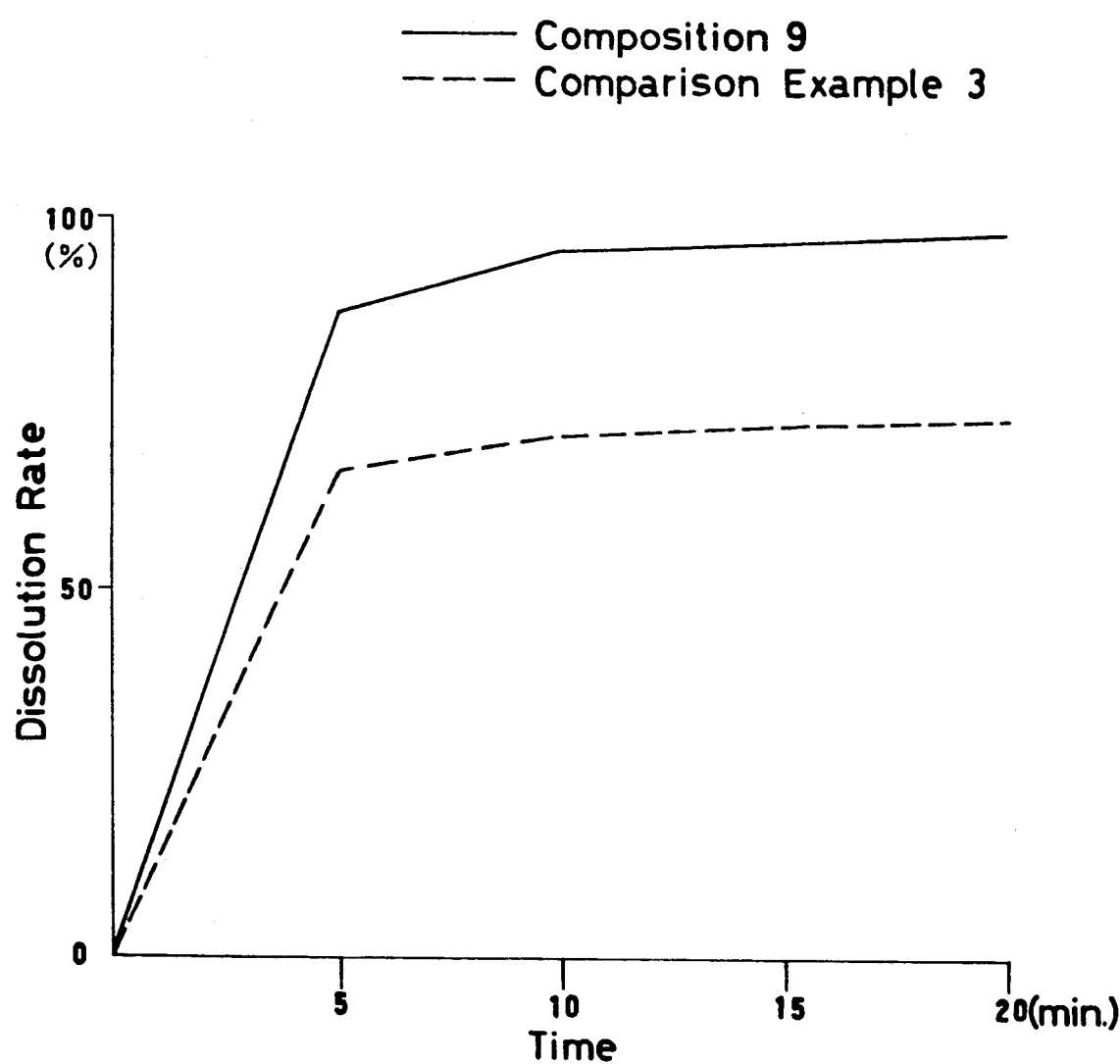
FIG. 2 shows, by graph, the results of dissolution tests of the compositions shown in other Examples of this invention.

A dissolution test was performed, in the same manner as in the aforementioned Example 1, for each of the powder of Composition 9 and the powder of Comparison Example 3, and the results obtained are as shown in FIG. 2. As is clear from these results, the powder of Comparison Example 3 was slightly soluble, while the powder of Composition 9 showed a good dispersibility in water.

EXAMPLE 3

(13) Composition 10, containing an extract obtained by extraction with a water-containing organic solvent In 100 g of Platycodon fluid extract (Japanese Pharmacopoeia, solid content 15 w/v %), was dissolved 15 g of gum extracted from tamarind seeds, and then the solvent in the solution was distilled off by the spray-drying method, whereby a composition in powder form was obtained.

(14) Composition 11, containing an extract obtained by extraction with a water-containing organic solvent The procedure mentioned in (13) above (Composition 10) was followed except for using 10 g of the gum extracted from tamarind seeds in place of 15 g of the gum extracted from tamarind seeds, and adding 60 g of hexaglycerin monolaurate.

(15) Comparison Example 4

The solvent in 100 g of Platycodon fluid extract (Japanese Pharmacopoeia, solid content 15 w/v %) was distilled off by the spray-drying method, whereby a powder product was obtained.

EXAMPLE 4

(16) Composition 12, containing an extract obtained by extraction with a water-containing organic solvent In 100 g of Scopolia extract (Japanese Pharmacopoeia, total alkaloids 1.0%), was dissolved 5 g of gum arabic, and then the solvent in the solution was distilled off by the spray-drying method, whereby a composition in powder form was obtained.

(17) Composition 13, containing an extract obtained by extraction with a water-containing organic solvent The procedure mentioned in (16) above (Composition 12) was followed except for using 50 g of decaglycerin monostearate instead of 5 g of gum arabic.

(18) Comparison Example 5

The solvent in 100 g of Scopolia extract (Japanese Pharmacopoeia, total alkaloids 1.0%) was distilled off by the spray-drying method, whereby a powder product was obtained.

Dissolution test

Figure 3:
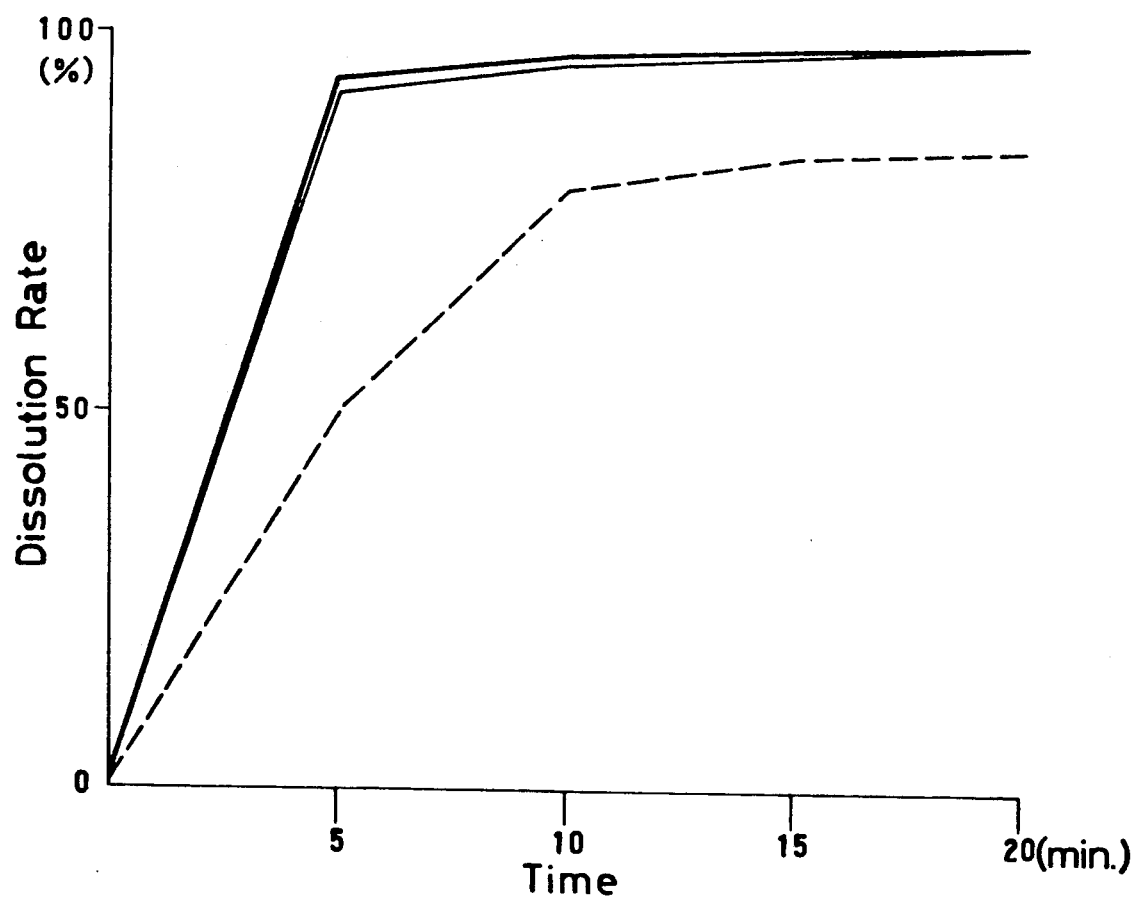
FIGS. 3 and 4 show, by graph, the results of dissolution tests of compositions shown in further Examples, other than the above, of this invention.
Figure 4:
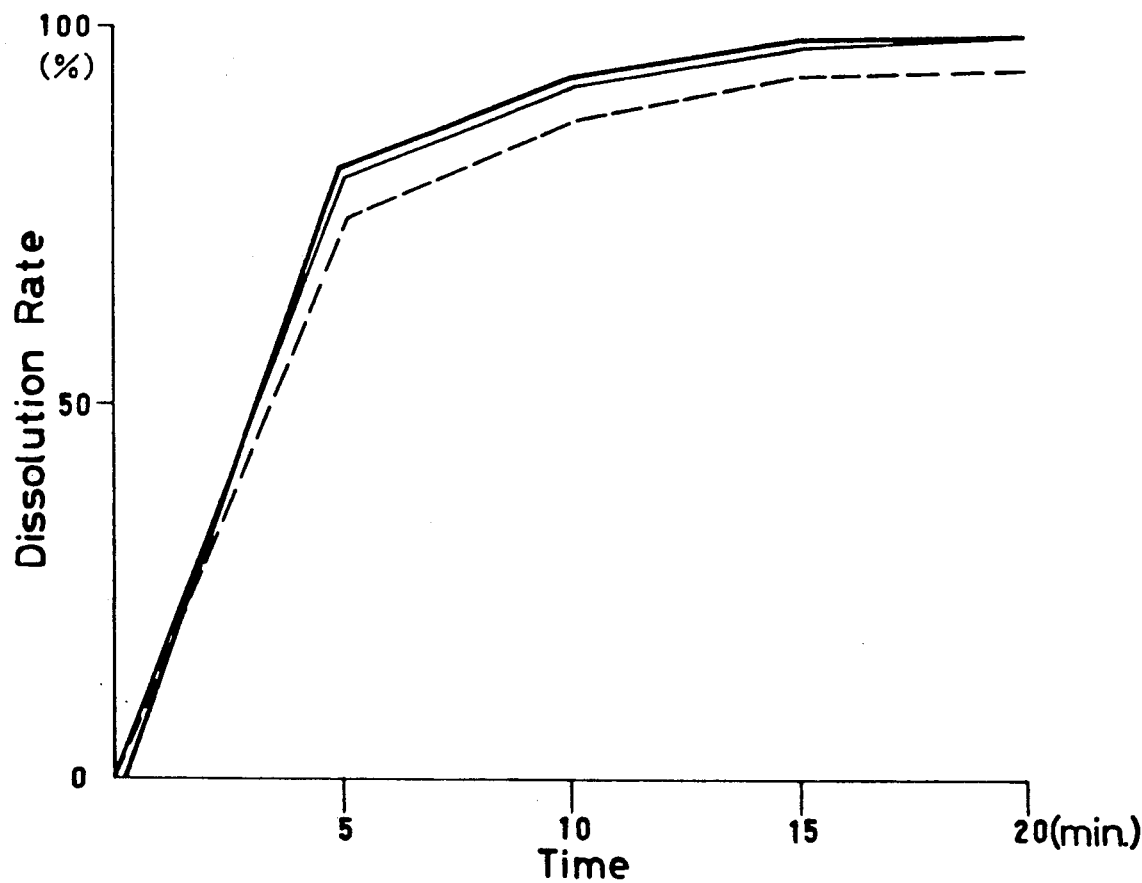

A dissolution test was performed, in the same manner as in Example 1, for each of the powders of Compositions 10-13, and powders of Comparison Examples 4 and 5, and the results are shown in FIGS. 3 and 4. It is to be noted that the dissolution rate shown in FIG. 4 for Compositions 12 and 13 and Comparison Example 5 shows the dissolution rate of total alkaloids.

As is clear from these results, the powders of Compositions 10-13 each showed better dispersibility in water as compared with powders of Comparison Examples 4 and 5.

As mentioned above, the solid preparations, such as tablets, granules and powder preparations; and non-alcoholic liquid preparations such as drinkable preparations and syrups, which are made from the compositions of this invention are well absorbed into the digestive tract and thus show a high bioavailability, although no alcohol is contained. Therefore, these preparations are most suitable for the treatment of disorder in cerebral circulation in the elderly people and minors, and also in patients with liver diseases.

What is claimed is:

1. A water-soluble composition which comprises;
   (a) as an active ingredient a pharmaceutically effective amount of a flavone glycoside or biflavone from Ginkgo leaf by extraction with a water-containing organic solvent, selected from the group consisting of water-containing methanol, water-containing ethanol, water-containing acetone, or water-containing methyl ethyl ketone, and a carrier which comprises at least one of
   (b) a water-soluble high-molecular weight substance selected from the group consisting of gum arabic, xanthan gum, guar gum, gum extracted from tamarind seeds and sodium alginate; and
   (c) a fatty acid ester of polyglycerol selected from the group consisting of decaglycerin monostearate, hexaglycerin monostearate, hexaglycerin monooleate, hexaglycerin monolaurate, and tetraglycerin monolaurate, provided the hydrophil lipophil balance of the ester is 10 or higher.

2. A process for preparing a water-soluble composition containing as a water-insoluble extract a flavone glycoside or biflavone obtained by extraction from Ginkgo leaf with a water-containing organic solvent, selected from the group consisting of water-containing methanol, water-containing ethanol, water containing acetone, or water-containing methyl ethyl ketone, comprising:
   obtaining said extract
   dissolving said extract and at least one of
   (a) a water-soluble high molecular weight substance selected from the group consisting of gum arabic, xanthan gum, guar gum, gum extracted from tamarind seeds and sodium alginate, and
   (b) a fatty acid ester of polyglycerol, selected from the group consisting of decaglycerin monostearate, decaglycerin monooleate, decaglycerin monolaurate, hexaglycerin monostearate, hexaglycerin monooleate, hexaglycerin monolaurate, and tetraglycerin monolaurate provided the hydrophil lipophil balance of the ester is 10 or higher;
   in a water-containing lower alcohol, and
   distilling off said alcohol.

3. A process for preparing a water-soluble composition containing, as a water-insoluble extract, flavone glycoside or biflavone obtained by extraction from Ginkgo leaf with a water-containing organic solvent selected from the group consisting of water-containing methanol, water-containing ethanol, water-containing acetone, or water-containing methyl ethyl ketone, comprising:
   obtaining said extract, and
   structurally modifying a surface of the extract by coating with a water-soluble high molecular weight substance selected form the group consisting of gum arabic, xanthan gum, guar gum, gum extracted from tamarind seeds and sodium alginate; and a fatty acid ester of polyglycerol selected from the group consisting of decaglycerin monostearate, decaglycerin monooleate, decaglycerin monolaurate, hexaglycerin monostearate, hexaglycerin monooleate, hexaglycerin monolaurate, and tetraglycerin monolaurate provided the hydrophil lipophil balance of the ester is 10 or higher.

4. A water-soluble composition obtained by the method of claim 3.

5. A process for preparing a water-soluble composition containing, as a water-insoluble extract, flavone glycoside or biflavone obtained by extraction from Ginkgo leaf with a water-containing organic solvent selected from the group consisting of water-containing methanol, water-containing ethanol, water-containing acetone, or water-containing methyl ethyl ketone, comprising:
   obtaining said extract, and
   dissolving said extract and at least one of
   (a) a water-soluble high molecular weight substance selected from the group consisting of gum arabic, xanthan gum, guar gum, gum extracted from tamarind seeds and sodium alginate; and
   (b) a fatty acid ester of polyglycerol selected from the group consisting of decaglycerin monostearate, decaglycerin monooleate, decaglycerin monolaurate, hexaglycerin monostearate, hexaglycerin monooleate, hexaglycerin monolaurate, and tetraglycerin monolaurate, provided the hydrophil lipophil balance of the ester is 10 or higher; in a water-containing lower alcohol;
   absorbing a thus-obtained solution or emulsion to an excipient in a fluidized bed; and
   drying the excipient which absorbed the solution or emulsion.

6. A water-soluble composition obtained by the method of claim 5.

* * * * *